United States Patent [19]

Wilson et al.

[11] 4,357,339

[45] Nov. 2, 1982

[54] CONTROL OF PINE BEETLES WITH 1,5-DIMETHYL-6,7-DIAZABICYCLO[3.2.1]OCT-6-ENE

[75] Inventors: R. Marshall Wilson, Cincinnati, Ohio; John W. Rekers, Spartanburg, S.C.

[73] Assignee: Research Corporation, New York, N.Y.

[21] Appl. No.: 218,629

[22] Filed: Dec. 22, 1980

Related U.S. Application Data

[62] Division of Ser. No. 140,206, Apr. 14, 1980, Pat. No. 4,291,051.

[51] Int. Cl.$^3$ .............................................. A01N 43/56
[52] U.S. Cl. .................................. 424/273 P; 548/369
[58] Field of Search ..................... 548/369; 424/273 P

[56] References Cited

PUBLICATIONS

Wilson et al. I, Abstract, Apr. 1979 meeting of the American Chemical Society, Hawaii.
Wilson et al. II, J. Am. Chem. Soc. 1979, vol. 101, pp. 4005-4007.
Wilson et al. III, J. Am. Chem. Soc. 1978, vol. 100, pp. 225-226.
Renwick, Boyce Thompson Institute Contributions, 1970, vol. 24, pp. 337-341.

*Primary Examiner*—Henry R. Jiles
*Assistant Examiner*—N. Harkaway
*Attorney, Agent, or Firm*—Wyatt, Gerber, Shoup, Scobey & Badie

[57] ABSTRACT

1,5-Dimethyl-6,7-dioxabicyclo[3.2.1]-octane and 1,5-dimethyl-6,7-diazabicyclo[3.2.1]-oct-6-ene are synthesized. They are analogs of the western and southern pine beetle natural-pheromone, frontalin. They are useful for controlling the multiplication of these harmful insects and for limiting infestation of wooded areas by them.

2 Claims, No Drawings

CONTROL OF PINE BEETLES WITH 1,5-DIMETHYL-6,7-DIAZABICYCLO[3.2.1]OCT-6-ENE

The invention described herein was made in the course of work under a grant or award from the National Science Foundation.

This is a division, of application Ser. No. 140,206 filed Apr. 14, 1980, now U.S. Pat. No. 4,291,051.

BACKGROUND OF THE INVENTION

Each year the western and southern pine beetles (*Dendroctonus brevicomis* LeConte and *Dendroctonus frontalis* Zimm) do enormous amounts of damage to the pine forests of North America. Therefore, a means of controlling these pests is highly desirable.

The mass attacks on host trees by these insects is known to be guided at least in part by pheromones elicited by the insects. These pheromones act as aggregating agents to attract other beetles of the species to a food supply and to mating opportunities. Exploitation of the insects reliance upon an aggregation pheromone to bring the sexes together offers intriguing possibilities for insect control.

The pheromones initially direct the insects to weakened trees which they attack in mass and kill before moving on to destroy healthier trees. Additionally, the pheromones assure a high concentration of beetles in a relatively confined area and hence increase the chances of successful mating.

Pheromones have been used successfully in traps to control the explosive growth of *Ips typographus* in Norway and Sweden. In these countries, the insect pheromone was dispersed in small quantities from plastic tubes placed in the infested area. The insects were attracted inside the tubes which were constructed in such a way that they could not escape.

This procedure, however is not totally satisfactory for a number of reasons. The principal reason is that a large number of traps are required and their successful dispersion in a target area requires the work of many people.

In accordance with this invention, synthetic pheromones are provided which block or destroy the beetles pheromone receptor site so that the affected insect is no longer attracted to other beetles by the natural pheromone. The proximate effect is that the beetles are dispersed rather than concentrated. The ultimate effects are that the beetles feed on a large number of trees without lethal effects on any one, and the number of opportunities for successful mating are greatly reduced. The insect population is not destroyed. Instead, it is controlled. This is important because the insects contribute to the ecological balance of the forest. Their complete elimination would concurrently remove a valuable food source for the bird population.

THE INVENTION

The natural pheromone of the southern and western pine beetle is 1,5-dimethyl-6,8-dioxabicyclo[3.2.1]octane, or to use its more common name, frontalin. Frontalin is represented by the structural formula:

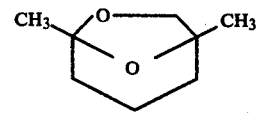

The compounds of this invention are 1,5-dimethyl-6,7-dioxabicyclo[3.2.1]-octane (peroxide) and 1,5-dimethyl-6,7-diazabicyclo[3.2.1]oct-6-ene (azo compound). They may be represented by the structural formulas:

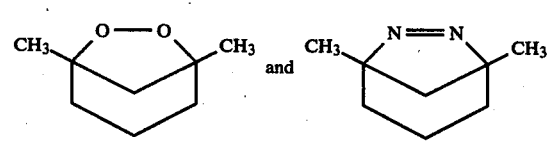

These compounds have proved to be remarkably effective as synthetic pheromones which disrupt the natural pheromone activity and disperse the beetles rather than concentrate them.

It will appear from the results to be described in more detail below that the azo compound is more active than the peroxide. However, the long term effect of the peroxide may be more significant. It appears that this synthetic pheromone is somewhat unstable and slowly rearranges to the natural pheromone, frontalin. Thus, as it slowly diffuses away from the release site in a target area, the relative concentration of frontalin to peroxide increases on the ever widening periphery of the area. As a result, the insect population responding to the natural pheromone becomes increasingly dispersed. Even as the population becomes dispersed there is a concentration, albeit a decreasing concentration, of peroxide on the periphery. Upon exposure to this material, a certain number of the beetles suffer permanent damage to their receptor sites.

The compounds of this invention are useful because (1) they function as aggregation pheromones in a manner similar to the action of frontalin, and (2) they disrupt natural activities of the insects apparently by binding to the frontalin receptor sites. This binding may be irreversible, but most likely is a reversible reaction with the equilibrium strongly favoring binding rather than release. It will be recognized that even if the equilibrium favored release, there would still be a period of time during which the activity of frontalin would be inhibited. To the extent that the natural activity is inhibited, the growth of the insect population is controlled and the forest is protected from infestation.

It is surprising to find that the peroxide and the azo compound function as insect attractants. Renwick in an article in Boyce Thompson Inst. Contrib. 24 337 (1971), reports the results of a study of a large number of analogs of frontalin as insect attractants. He found that all except one were completely inactive. He concluded, "The unique structure of frontalin, therefore, seems to be critical, and it is unlikely that any other configuration would be as effective in attracting the southern pine beetle.", page 338 second column to page 339, first column. The analogs of frontalin which Renwick included in his study were the 5-methyl-, 1-methyl-, 1,4,-dimethyl-, and 5-7-dimethyl-compounds.

The ability of the peroxide and the azo compound to saturate the receptor sites so that they were not available for reaction with frontalin was tested by the procedure of Birch and Light as reported in the J. Insect Physiol. 25 161 (1979) and Naturwissenschaften 66, S 159 (1979).

In this procedure, a beetle antenna to be tested is placed in a circuit with an oscilloscope. Air saturated with the material to be tested is blown over the antenna and the response noted. For example, for testing the peroxide against frontalin the procedure is as follows:
(1) Blow frontalin over the antenna and record the electrical response.
(2) Blow the peroxide over the antenna. If the frontalin has saturated the receptor sites, there should be no electrical response.
(3) Repeat the experiment in reverse. If the peroxide saturates the receptor sites, there should be no response to frontalin. To the extent that there is an electrical response, the peroxide has failed to saturate the receptor sites.

The following table shows the extent to which the material in column 1 saturates an antenna so that the receptor sites are not available for reaction with the material of column 2 when antennae from male and female bettles were tested.

TABLE 1

| 1 | 2 | MALE | FEMALE |
|---|---|---|---|
| Peroxide | Frontalin | 57.14 | 50.00 |
| Peroxide | Frontalin | 67.95 | 61.54 |
| Azo Compound | Frontalin | 88.64 | 75.00 |
| Frontalin | Peroxide | 48.15 | 50.00 |
| Frontalin | Azo Compound | 38.48 | 55.88 |
| Azo Compound | Peroxide | 100.00 | 80.95 |
| Azo compound | Peroxide | 87.50 | — |

It will be observed that both the peroxide and the azo compound are remarkably effective in binding receptor sites, and that the activity of the azo compound in direct competition with the peroxide is especially high.

One procedure for preparing the compounds of this invention is by conversion of 6-methyl-6-heptene-2-one tosylhydrazone to the azo compound with boron tetrafluoride etherate followed by subjecting the azo compound to the action of a laser in the presence of a photosensitizer with a triplet energy above about 60 Kcal/mole.

The peroxide can be directly prepared from 6-methyl-6-heptene-2-one by treatment with boron trifluoride etherate in the presence of hydrogen peroxide.

The ketone is prepared by an oxy-Cope rearrangement of the corresponding alcohol in the presence of the cyclic ether 18-crown-6 and a base such as potassium hydride. This is converted to the tosylhydrazone by reaction with the corresponding hydrazine.

The preparation of the azo compound takes place in a reaction inert organic solvent, suitably a halogenated hydrocarbon solvent containing up to two carbon atoms at a temperature of from 0° C. to 30° C. over a period of from about 0.5 to 4 hours. To insure as complete a reaction as possible, a molar excess of the boron trifluoride etherate is employed. It is preferred to initiate reaction at a low temperature, e.g. 0° C. to 5° C. and complete it at about 25° C. to 30° C.

The direct cyclization of the ketone is also effected in a similar inert organic solvent using a molar excess to the boron trifluoride etherate. However, the reaction period at the higher temperature level is somewhat extended. It may be as long as 15 to 24 hours. The temperature is from about −80° C. to 25° C.

The active compounds of this invention may be dispersed for the control of beetles by any of the standard procedures used in the art. The compounds may be used along or with a coniferously acceptable carrier. The optimum procedure is to spray the material at the leading edge of a blighted area, for example in microencapsulated particles. Optimally, the capsules will have various wall thickness so as to provide a time release effect. The products may be encapsulated without any additives, or they may be encapsulated in a solvent, e.g. a hydrocarbon solvent. Microencapsulation may be effected by standard procedures well known in the art.

An effective amount of active material employed for the control of an infected area will vary appreciably. Even extremely small amounts will have some control action. There is no advantage to spreading high concentrations since the costs required do not compensate for the results. As a general rule, from about 1 to 3 grams of relatively pure material per acre or 2 to 10 grams per acre of encapsulated material will be sufficient to exercise effective control.

The following non-limiting examples are given by way of illustration only.

EXAMPLE 1

6-Methyl-6-Heptene-2-One

To a solution of 14.28 g (54.4 mmol) of 18-crown-6 and 10.00 g (79.4 mmol) of 3,5-dimethyl-1,5-hexadien-3-ol in 300 mL of anhydrous THF under a nitrogen atmosphere was added 13.93 g of 24.5% KH suspended in mineral oil (85 mmol). The resulting dark orange solution was refluxed for 1 h, cooled, and quenched with 150 g of ice. Following saturation of the aqueous layer with NaCl, the reaction mixture was extracted with ether (3×100 mL). The combined organic layers were washed with water (100 mL) and dried, and the solvent was removed at 5°–10° C. The dark yellow residue was distilled to afford 6-methyl-6-hepten-2-one(5a): bp 49°–50° C. (8.5 mm); 7.79 g (61.8 mmol, 78%); IR (neat) 1713 cm$^{-1}$; NMR ($\delta$CDCl$_3$) 1.4–2.7 (6H, m), 1.72 (3H, m) 2.13 (3H, s), 4.70 ppm (2H, bs).

EXAMPLE 2

The Tosylhydrazone

The above ketone was added to a stirred suspension of about 1.1 equiv of tosylhydrazine and 1 drop of acetic acid in n-pentane. Upon stirring for 24 h the solid was collected by filtration and washed with n-pentane. A single recrystallization from EtOH at −78° C. afforded the tosylhydrazone as a mixture of syn and anti isomers (ca 1:9); mp 81.5°–82.5° C.; IR (KBr) 3220, 1645, 1593, 1340, 1168 cm$^{-1}$; NMR ($\delta$CDCL$_3$) 1.2–2.4 (6H, m), 1.65 (3H, bs), 1.78 (3H, s)anti [1.91(s) syn], 2.44 (3H, s) 4.53–4.80 (2H, m), 7.32 (2H d, J=8 Hz), 7.90 (2,H,d. J=8 Hz), 7.5–8.3 ppm (1H, b). Anal. (C$_{15}$H$_{22}$N$_2$SO$_2$) C, H, N.

EXAMPLE 3

1,5-Dimethyl-6,7-Diazabicyclo[3.2.1]Oct-6-Ene

To a solution of 3.126 g (10.6 mmol) of 6-methyl-6-hepten-2-one tosylhydrazone in 100 mL of anhydrous CH$_2$Cl$_2$ was added with stirring at 0° C. 1.84 g (13 mmol) of BF$_3$.Et$_2$O. The reaction mixture was allowed to warm to room temperature and stirred for an additional 2 h. The reaction mixture was concentrated by removing solvent through a distillation column. The yellow residue was dissolved in 40 mL of ether and the ethereal solution extracted with 1 M $K_2CO_3$ (3×10 mL). The combined aqueous washings were extracted further with ether (2×10 mL) and the combined ethereal extracts dried by filtration through $MgSO_4$. The solvent was removed by distillation through a column and the azoalkane obtained from the residue by a trap-to-trap distillation (0.025 mm). A second Kugelrohr distillation (130°–140° C., 1 atm) afforded the pure (99% by GLC) azoalkane; 1.273 g (9.22 mmol, 87%); IR (neat) 1520 cm$^{-1}$; NMR ($\delta CDCl_3$) 0.9–1.7(8H,m), 1.60 ppm (6 H,s); UV (n-pentane) 351 nm ($\epsilon$192). Anal ($C_8H_{14}N_2$)C, H, N.

EXAMPLE 4

1,5-Dimethyl-6,7-Dioxobicyclo[3.2.1]Octane

Method A

A Freon-11 ($CFCl_3$) solution of benzophenone (0.3 mmoles) and 0.2 mmmoles of the product of the previous example was placed in a Griffin-Warden tube under 60–90 psi of $O_2$ and cooled to $-20°$ C. to 0° C. with an aluminum jacket through which methanol was circulated. The solution was irradiated with 363.8 nanameters (0.4–0.6 watts) of an argon ion laser for about 0.7 watt-hours per mmole of azo compound (e.g. the complete reaction of 3.6 mmoles of azo compound requires about 5 hours of irradiation with a laser output of about 0.5 watts). The solvent was removed at 0° C. under reduced pressure to afford a viscous yellow oil. NMR analysis of this oil indicates a crude yield of 50–60% of the title compound.

Chromatography of this oil on silica gel (10 g. silica gel per mmole of title compound) and elution with $CH_2Cl_2$ provided the desired product contaminated with benzophenone.

The solvent was removed at 0° C. under reduced pressure and the oily residue distilled with a Kugelrohr apparatus at 70° C. to 80° C. and about 10–15 mm Hg to give the product in 90% purity as judged by vapor chromatography. Yield 20–35%.

The same result is achieved when the benzophenone is replaced with another sensitizer such as thiozanthone.

Analytical sample prepared by vapor phase chromatography on a 10 ft. by 0.25 inch Teflon coated Al tube packed with 15% SE-30 on Chromsorb P AW-DMCS, 80–100 mesh with on column injection at 119° C. with a helium flow rate of 88CC/min. (Retention time=17 min); IR (neat) 1448,1370, 1343, 1235, 1164 and 854 cm$^{-1}$, NMR ($\delta CDCl_3$) 1.3 PPM (6H, s), mass spectrum m/l M$^+$=142. Anal.($C_8H_{14}O_2$): Calc. C, 67.57; H, 9.92. Found C, 67.58; H, 10.05.

Method B

To 90% $H_2O_2$ (0.75 ml.) at $-78°$ C. under a nitrogen atmosphere was added 35 ml of $CHCl_2$ and 1.60 ml (1.84 g, 1.30 mmole) of $BF_3.Et_2O$ followed by 6-methyl-6-heptene-2-one (0.844 g, 6.69 mmole) over a period of 2 minutes with stirring. The cooling bath was removed and stirring continued for 20 hours at room temperature. The crude reaction mixture was washed with water (2×25), 5% $NaHCO_3$ (1×25), dried over $MgSO_4$ and the solvent removed under reduced pressure at 0° C. The colorless oil which remained was chromatographed on 35 g of silica gel and eluted with $Ch_2Cl_2$. The residue remaining on evaporation of the appropriate chromatography fractions, as determined by thin layer chromatography with known samples, was distilled in a Kugelrohr apparatus at 95°–105° C. at 25–30 mm Hg to afford 0.680 g (72% yield) of the desired product which is homogeneous by vapor phase chromatography and identical to the material prepared by Method A.

Single Kugelrohr distillation of the crude reaction mixture yields a 97–98% pure product as judged by vapor phase chromatography.

What is claimed is:

1. A composition for the control of pine beetles comprising an effective amount of 1,5-dimethyl-6,7-diazabicyclo[3.2.1]oct-6-ene together with a coniferously acceptable carrier.

2. A method of limiting the infestation of a wooded area by western or southern pine beetles comprising treating the infested area with an effective amount of 1,5-dimethyl-6,7-diazabicyclo[3.2.1]oct-6-ene.

* * * * *